(12) United States Patent
Nash et al.

(10) Patent No.: US 8,157,787 B2
(45) Date of Patent: Apr. 17, 2012

(54) INTERVENTIONAL PROCEDURE DRIVE AND CONTROL SYSTEM

(75) Inventors: John E. Nash, Chester Springs, PA (US); Gregory Walters, Malvern, PA (US); Stephen Heiman, Exton, PA (US); Jim Barnitz, Schwenksville, PA (US); Pete Fatone, Exton, PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

(21) Appl. No.: 13/211,015

(22) Filed: Aug. 16, 2011

(65) Prior Publication Data
US 2012/0004601 A1 Jan. 5, 2012

Related U.S. Application Data

(63) Continuation of application No. 10/253,034, filed on Sep. 24, 2002, now Pat. No. 7,998,107.

(51) Int. Cl.
*A61M 31/00* (2006.01)
(52) U.S. Cl. .............................. 604/506; 604/43; 604/35
(58) Field of Classification Search .............. 604/30–35, 604/43, 66, 67, 73, 131, 151, 152, 506, 514; 606/107
See application file for complete search history.

(56) References Cited

U.S. PATENT DOCUMENTS

| | | | |
|---|---|---|---|
| 3,684,405 A | 8/1972 | Wright et al. | |
| 4,180,074 A | 12/1979 | Murry et al. | |
| 4,552,552 A | 11/1985 | Polaschegg et al. | |
| 4,604,089 A | 8/1986 | Santangelo et al. | |
| 5,191,878 A | 3/1993 | Iida et al. | |
| 5,242,404 A | 9/1993 | Conley et al. | |
| 5,360,398 A | 11/1994 | Grieshaber et al. | |
| 5,531,681 A | 7/1996 | Walton et al. | |
| 5,630,799 A | 5/1997 | Beiser et al. | |
| 5,697,898 A | 12/1997 | Devine | |
| 5,813,842 A | 9/1998 | Tamari | |
| 5,879,361 A | 3/1999 | Nash | |
| 6,024,720 A | 2/2000 | Chandler et al. | |
| 6,258,061 B1 | 7/2001 | Drasler et al. | |
| 6,986,753 B2 | 1/2006 | Bui | |
| 2002/0019607 A1 | 2/2002 | Bui | |

FOREIGN PATENT DOCUMENTS
WO WO-02/24252 A2 3/2002

*Primary Examiner* — Laura Bouchelle
(74) *Attorney, Agent, or Firm* — Jeffrey R. Ramberg

(57) ABSTRACT

A pumping system for use in medical applications where liquids must be infused and aspirated from a mammalian patient, and whose economics are such that it is cost effective to simply dispose of it after a single use. The system features positive displacement pump(s) such as reciprocating pump(s) containing a damping mechanism to dampen out the peaks and valleys in the fluid pressure that is pumped, which is important for preventing cavitation. The system furthermore features a shut-off valve on the extraction side so that certain injected fluids such as contrast medium, are not immediately pumped out of the patient. In a preferred embodiment, the system also features means for independently controlling the fluid pressure/volume on the infusion and extraction sides, self-priming capability, a continuous fluid path, and visual air bubble detection, with viewports located at important points in the fluid path, such as at pumps and valves.

20 Claims, 5 Drawing Sheets

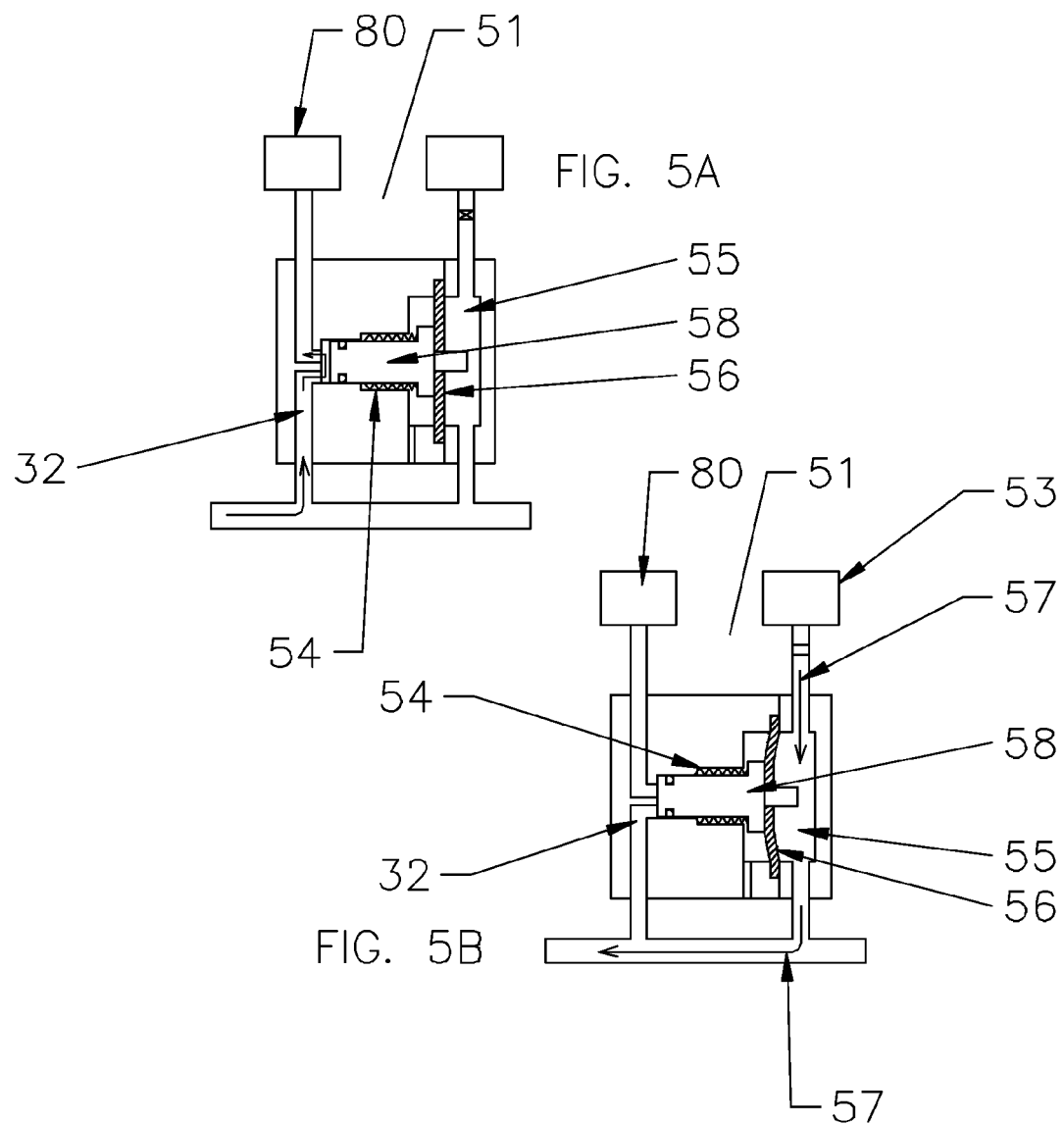

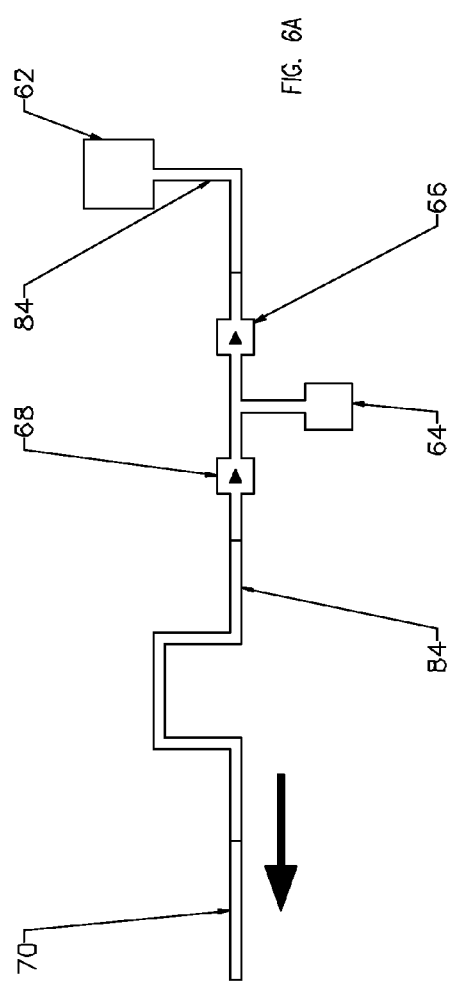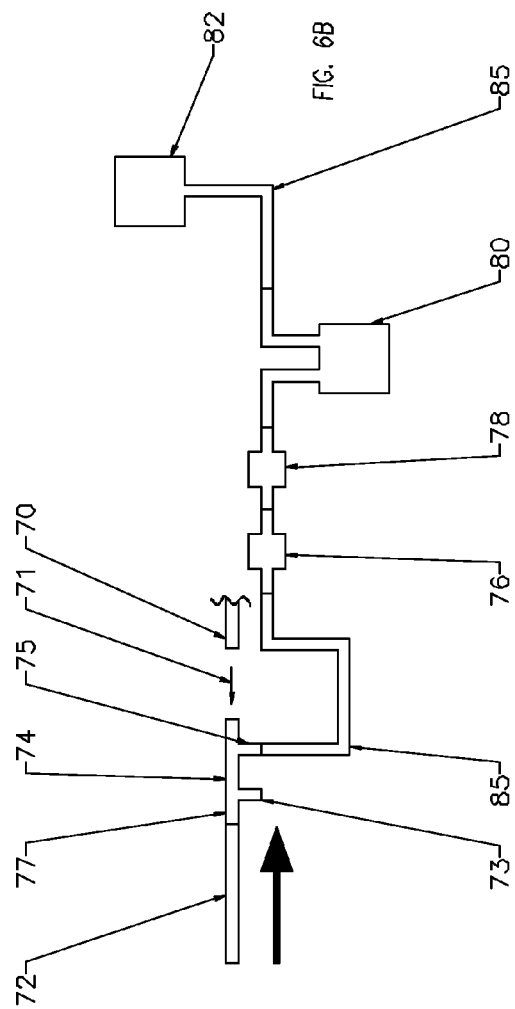

INTERVENTIONAL PROCEDURE DRIVE AND CONTROL SYSTEM

CROSS REFERENCE TO RELATED APPLICATIONS

This application is a Continuation Application of our earlier filed U.S. patent application Ser. No. 10/253,034, filed on Sep. 24, 2002, now U.S. Pat. No. 7,998,107, entitled Interventional Procedure Drive and Control System, which is assigned to the same assignee as this invention and whose disclosures are incorporated by reference herein.

BACKGROUND OF THE INVENTION

1. Field of the Invention

The invention generally relates to medical devices and procedures where fluids preferably are simultaneously infused and aspirated from the patient. The invention more particularly concerns a multi-use, or preferably a single-use pumping system, to infuse and aspirate liquids to and from a surgical site through a catheter, conduit or tube.

2. Description of Related Art

The use of pumping mechanisms to flush debris created during diagnostic and therapeutic procedures is not new, see for example U.S. Pat. No. 6,258,061 (Drasler), and U.S. Pat. No. 5,879,361 (Nash). These inventions describe using a catheter for clearing an occluded blood vessel, by using either a rotating impact head, coupled with a flushing mechanism (Nash) or using high pressure jets of fluid to clear the thrombus (Drasler).

Nash discloses the use of peristaltic pumps as the infusion and extraction pumps (Nash). Peristaltic pumps have a number of attributes that account for their widespread use in medical applications. The pumps are accurate in metering flow over a range of pressures. The maximum and minimum variations in flow rate during a pump cycle do not vary too greatly from the mean flow rate. The fluid pathway (e.g., a tube) of the pumps is easily sterilized and visible. When not in operation, there is very little if any leakage through the peristaltic pump head.

On the other hand, peristaltic pumps are relatively energy inefficient, thereby requiring AC power or large batteries as their power supply. In fact, the pumping system that uses such pumps is usually sufficiently large that it will not fit within the confines of the "sterile field" of the operating room. Thus, such a pump system typically is located at a remote region of the operating room, distant from the doctor, who must then direct another person to actually operate, or at least monitor, the pump system.

Drasler discloses the use of jets to emulsify the thrombus in the blood vessel. The high pressure jets as described are generated "with a positive displacement pump, such as a piston pump . . . " which is designed to be disposable for sanitary reasons (Drasler). The pump can operate under pulsatile or steady flow. The invention described by Drasler may allow the fluid to exhaust by directing the spray of the catheter inlet back towards the exhaust outlet of the catheter, or alternatively "a vacuum pump to provide for removal of the fragmented thrombus or tissue, or a roller pump may be used to accomplish a similar effect."

The Drasler inventions pertain to high pressure applications, such as cutting and emulsifying thrombi using liquid jets. When the medical intervention pertains to other treatments such as infusion of a diagnostic agent or a therapy, however, such single cylinder reciprocating pumps, by their design, result in large variations in instantaneous flow rate during a pump cycle. The fluctuations in the instantaneous flow rate range from a minimum flow rate of zero to a maximum that is a number of times greater than the mean flow rate. The fluctuating flow rate has a pronounced impact on the pressure in the aspiration.

The variations in instantaneous flow rate as a result of the back and forth motion of the pump piston require the liquid in the conduit connecting the patient to the pump to be accelerated during increasing flow, and decelerated during decreasing flow. When aspirating fluids, the force required to accelerate the flow in the conduit results in a decreased pressure at the entrance to the pump. The variations in flow rate also increase the instantaneous frictional losses in the catheter because the frictional losses are related to the square of the flow's velocity. The frictional losses at peak instantaneous flows are substantially higher than the losses associated with a steady flow at the mean flow rate. The force required to overcome the increased losses also results in a lower pressure at the pump entrance.

Both of the above effects are particularly troublesome in aspiration pumps since the minimum pressure at the pump is limited to the liquid's vapor pressure. If pressure falls to the liquid's vapor pressure, cavitation will occur (as the liquid boils) and aspiration will be impeded. Specifically, the evolving of vapor will render the actual extraction rate of liquid indeterminate. Further, if the system were to be shut off at that point, it is at least theoretically possible for an air bubble to be pushed back up the catheter into the patient, for example, if the aspiration pathway flow is reversed due to the introduction of drugs or contrast media, via activation of an injection port on a guide connector branch.

Another drawback associated with the reciprocating pump is leakage through the pump when it is stopped. The leakage occurs in the direction of flow and is due to the arrangement of the check-valves within the pump, which allow virtually unrestricted flow only in the intended direction. This drawback becomes problematic when the aspiration conduit is located in an elevated pressure environment such as an artery or the aspiration conduit is used as a pathway to introduce medication or other liquids when aspiration is stopped. Specifically, the arterial blood pressure can be sufficient to cause bleeding through the aspiration conduit, through the aspiration pump and into the aspiration or extraction bag.

The present invention addresses and solves these and other shortcomings of the prior art.

SUMMARY OF THE INVENTION

In spite of these inherent limitations of reciprocating-type pumps for medical applications, the efficiency and economics of such pumps are too attractive to ignore. Thus, it is an object of the present invention to provide an efficient and low cost substitute for peristaltic pumps in infusing and evacuating a fluid through a patient during a medical procedure on a living being.

It is an object of the present invention to provide infusion/evacuation pumps that are sufficiently compact as to be easily confined within the sanitized zone of a hospital operating room.

It is an object of the present invention to provide an infusion/evacuation pump whose economics are such as to justify disposing of the pump unit after just a single use.

It is an object of the present invention to provide a reciprocating type pump with a means for damping out the fluctuations in the aspiration pressure.

It is an object of the present invention to provide a means for preventing backflow into the aspiration pumping system.

It is an object of the present invention to provide a means for visually inspecting for air bubbles in the fluid pathway, particularly in the infusion fluid path.

It is an object of the present invention to provide a pumping system that is self-priming.

It is an object of the present invention to temporarily cease normal forward fluid flow through the fluid circuit, and to close off the aspiration path at a point beyond or after the catheter so that a diagnostic or therapeutic agent can be injected into the patient by way of an injection port in the catheter.

The pumping system of the present invention fulfills these and other objectives. Specifically, the pumping system of the invention utilizes non-peristaltic-type positive displacement pumps such as reciprocating pumps for flushing and extracting fluid through a catheter to clear debris. The invention furthermore features flow control devices such as a pulse damper and a shut-off valve, and a controller to manage the process. The combination of these features yields an infusion/aspiration circuit with all the desired attributes, including high efficiency, low cost and compact size.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 4a represents a diaphragm type damper. FIG. 4b represents an elastomeric tubing type damper. FIG. 4c represents a piston type damper.

FIGS. 5a and 5b are enlarged views, in section, of a pressure-activated shut-off valve. FIG. 5a represents the pressure-activated shut-off valve in the open position, allowing fluid flow to the aspiration pump. FIG. 5b represents the pressure-activated shut-off valve in the closed position, wherein the aspiration pump is inactive, and the injection of fluids, contrast agent or drugs, are added.

FIGS. 6a and 6b is a schematic diagram, shown as two parts, namely, as infusion and aspiration pathways, respectively, of the fluid pathway of the system. FIG. 6a represents the infusion pathway, with the flow of fluid from the reservoir bag towards the catheter, as shown by the direction of the large arrow. FIG. 6b represents the aspiration pathway, with the flow of fluid generally from the catheter towards the extraction bag, as shown by the direction of the large arrow.

DETAILED DESCRIPTION OF THE INVENTION AND PREFERRED EMBODIMENTS

Figure 1:
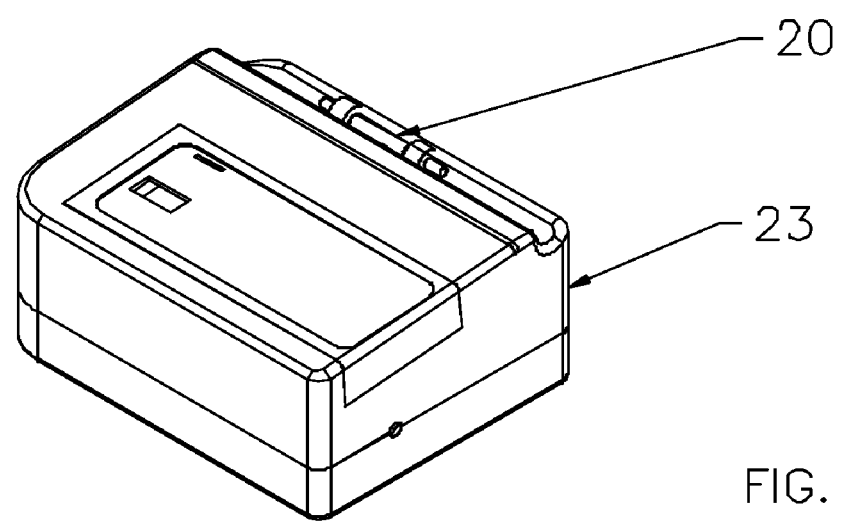
FIG. 1 is a schematic diagram of the pumping system of the invention, showing the visible arrangement of the external inlet and outlet check-valves of the infusion pump.

The objective of the invention is an infusion/aspiration pumping system that is compatible with the needs of a compact, single-use medical device for use in diagnostic and therapeutic treatments. The terms "aspiration" and "extraction" as used herein, are essentially synonymous. In a preferred embodiment, the system is suitable for use as a single-use device due to the incorporation of inexpensive non-peristaltic-type pumps, such as single cylinder reciprocating pumps, used in conjunction with other fluid control elements, to achieve flow attributes similar to that of a peristaltic pump design, yet at a much reduced cost and size. See FIG. 1. The reduced size of the invention, relative to the current state of the art system incorporating peristaltic pumps having similar flow capacities, allows the entire system to be contained within the sterile field of the operating room environment, therefore more accessible to the operating physician throughout the medical intervention procedure. The reduced cost of the reciprocating pumps allows a single-use design to be more cost effective, eliminating the need for cleaning and re-sterilization of the pumping mechanism after use.

The pumping system (see FIG. 2) of a preferred embodiment of the invention utilizes positive displacement pumps that may be capable of self-priming, such as reciprocating pumps to drive the flow of fluid for infusion 64 and aspiration 80 during a medical intervention procedure. The fluid control elements of the invention alter the flow attributes inherent in a reciprocating pump, by serving a damping function and a start/stop or valve function (to be discussed later), such that the flow is more suited for use in interventional medical procedures. Additionally, a preferred embodiment provides for a more visible pathway, with transparent viewports 20, such that the pathway may be visually inspected before and during use of the pumping system.

Again, one of the problems with reciprocating-type pumps is the variation or fluctuation in the pressure and flow rate of the medium being pumped, which often is undesirable in a medical intervention such as a catheterization. Thus, up to now, peristaltic pumps have been preferred for such procedures. The present invention addresses the fluctuating flow shortcoming of the single cylinder reciprocating pump by incorporating a compliant element (e.g., diaphragm 30, or damper spring 40 and damper piston 42, or elastomeric conduit 44, as shown in FIGS. 3 and 4a-4c) in the fluid pathway between the guide catheter 72 and the entrance to the aspiration pump 80 (as shown in FIG. 6b), to act as a pulse damper, smoothing the instantaneous flow rate in the conduit. The compliant element smoothes flow in the conduit by distorting a small distance (not shown) in response to an increase in fluid pressure. This has the effect of increasing the available volume for the fluid, thereby effectively storing liquid (and energy) from the conduit during the high pressure portion of the pump cycle. Conversely, when the fluid pressure falls, the compliant element moves in the opposite direction, effectively decreasing the available volume for the fluid, and thereby releasing liquid (and energy) to the system during the low pressure portion of the pump cycle. The compliant element could be a simple thin walled elastomeric conduit 44 or any other approach that creates a damping effect by increasing the available volume for liquid to reduce pressure, and vice-versa.

Figure 3:
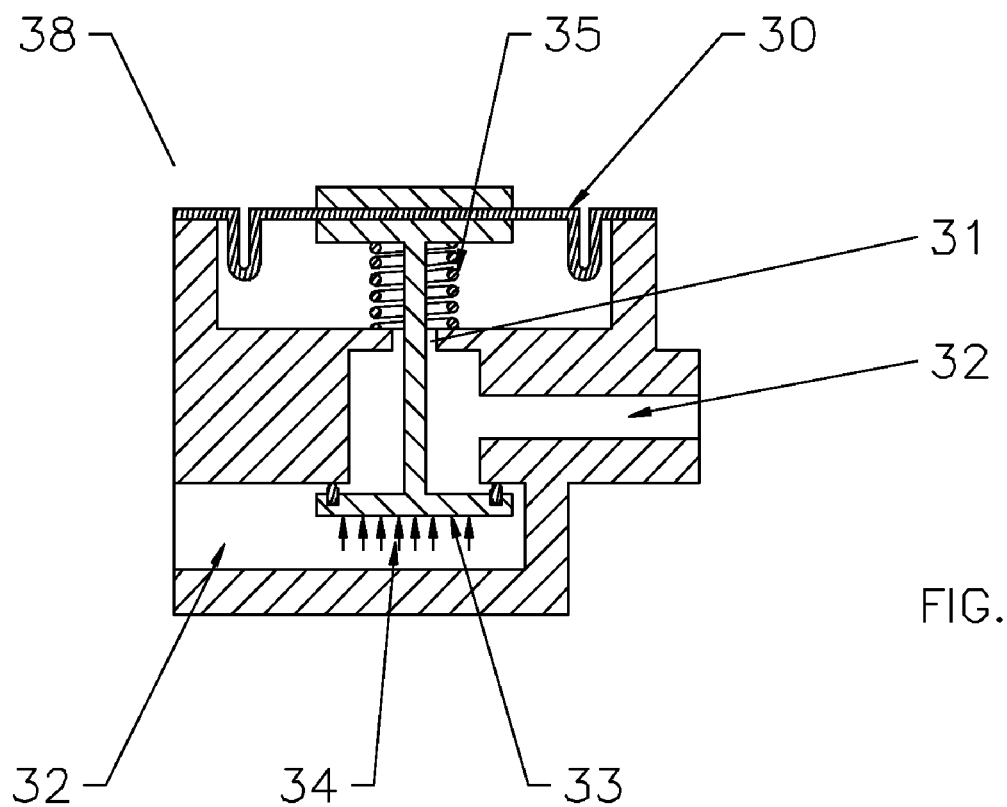
FIG. 3 is an enlarged view, in section, of a combined extraction shut-off valve and damper as described in an embodiment of the invention.

Recall the other problem with reciprocating pumps, i.e., the leakage problem. Again, when the system is de-energized and the pumps are stopped, there is still an open path for fluid in the forward direction through the fluid circuit. Thus, in an arterial intervention where an intra-arterial catheter is attached to the pump system, the patient's blood pressure could cause the patient to bleed continuously through the aspiration side of the circuit. A preferred embodiment solves the leakage problem of reciprocating pumps by adding a shut-off valve 38 or 51 (as shown in FIGS. 3, 5a and 5b, to be discussed later) at the entrance to the aspiration pump 80 (as shown in FIG. 6b). The valve 38 or 51 closes off the fluid pathway 32 when the aspiration pump 80 is stopped. The valve 38 or 51 can be actuated by a number of means, electronic, pressure level in the conduit or pressure level in the pump, or manual control. Actuation by pressure level in the conduit is particularly valuable because such a valve insures against excessive pressure buildup within the lumen of a vessel or other cavity of the patient, while preventing flow at lower pressures, such as the level of blood pressure typically generated on the arterial side of the cardiovascular system. Such valves are sometimes referred to as "pressure activated" valves.

In a preferred embodiment, such as that illustrated in FIG. 3, the shut-off valve 38 embodiment may also incorporate the features of a damping mechanism. This can be accomplished by a compliant element in the form of a diaphragm 30 exposed to atmospheric pressure, such that as the valve is open, the variations in the aspiration rate of flow through the fluid pathway 32 are minimized by the compliance of the diaphragm 30. When the aspiration pump 80 is inactive, the arterial pressure 34 from the body, in cooperation with the spring 35 closes the disk 33, thereby halting the aspiration through the fluid pathway 32. The shut-off valve 38 would reopen the fluid pathway 32 when the aspiration pump 80 is activated and vacuum is applied to both the diaphragm 30 and the disk 33. Vacuum is then transferred from the fluid pathway 32, to the diaphragm 30, via fluid bypass port 31. The larger area of the diaphragm 30, relative to that of the disk 33, would allow atmospheric pressure acting on the diaphragm 30 to overcome the spring 35 pressure and arterial pressure 34 acting on the disk 33, reopening and allowing extraction through the fluid pathway 32.

In another embodiment, namely that illustrated by FIGS. 5a and 5b, the shut-off valve 51 may be activated upon the injection of medication, contrasting agent, or other fluids 57, through the injection pathway 55. Valve 51 differs from valve 38 by, among other things, providing an injection pathway 55; which may be accessed through valve injection port 53. The shut-off valve 51 will close off the aspiration through the fluid pathway 32 as the injection of fluids 57 is made. This is desirable to prevent the flow of the injected fluid 57 directly to the extraction pump 80, rather than toward the patient. This is accomplished because the injection of fluids 57 causes increased pressure in the injection pathway 55, acting upon a valve diaphragm 56 and plunger 58, thereby compressing valve spring 54 allowing plunger 58 to halt the aspiration flow through the fluid pathway 32 leading to the aspiration pump 80. With this embodiment, an additional pressure activated valve (not shown) might be necessary to prevent flow of aspiration fluid along fluid pathway 32 due to the arterial pressure while the aspiration pump 80 is in an unpowered state. This pressure activated valve could be set to allow flow only after a certain line pressure or "cracking pressure" is achieved. This pressure could be set just above arterial pressure, such that the valve opens when aspiration pump 80 is energized.

The combination of a single cylinder reciprocating pump, pulse damper and shut-off valve yield an aspiration circuit with all the desired attributes including high efficiency, low cost and compact size.

For an infusion pumping circuit, single cylinder reciprocating pumps provide an attractive option with the exception of not being able to visually inspect the fluid pathway of the pump. Infusion devices that are used in the arterial or venous system need to provide protection against accidental air infusion. An effective and inexpensive means of protection is visual inspection of the fluid pathway prior to and during infusion.

Figure 2:
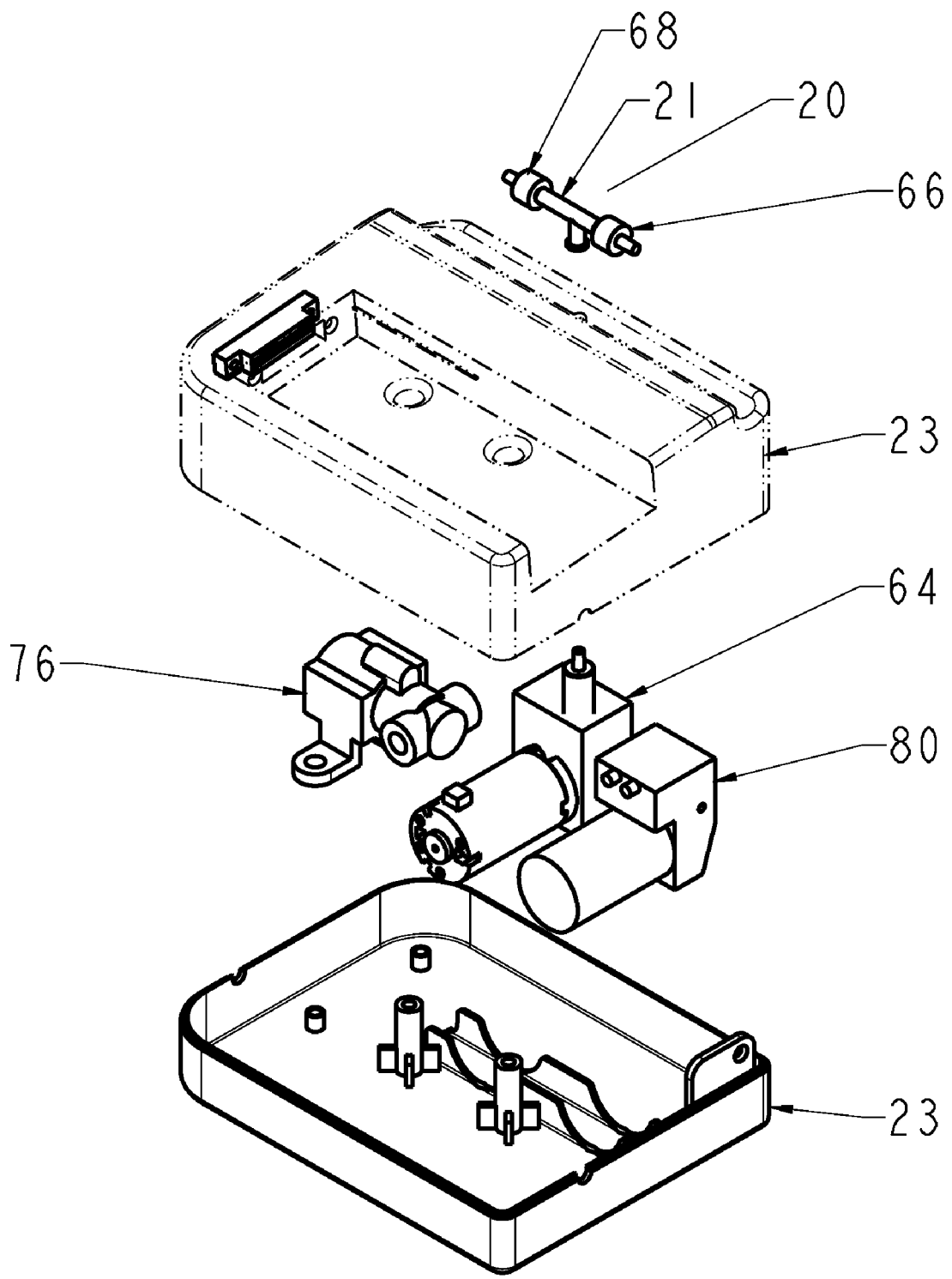
FIG. 2 is an exploded representation of the pumping system of the invention, showing the infusion pump, aspiration pump, and extraction shut-off valve, as contained within the housing.
Figure 4A:
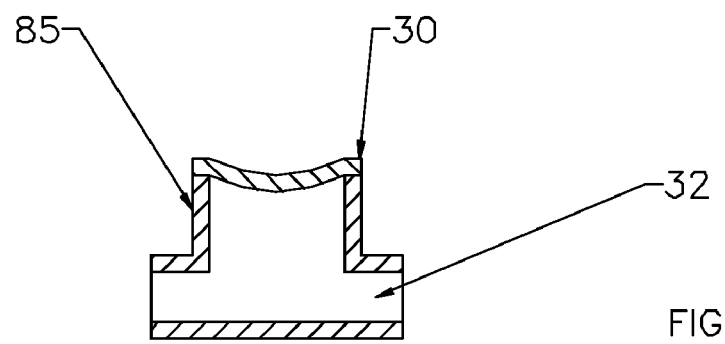
FIGS. 4a, 4b and 4c are enlarged views, in section of pulse dampers.
Figure 4B:
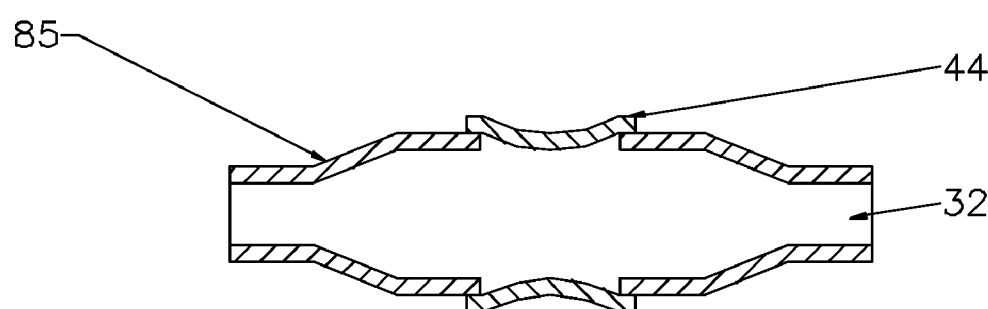
Figure 4C:
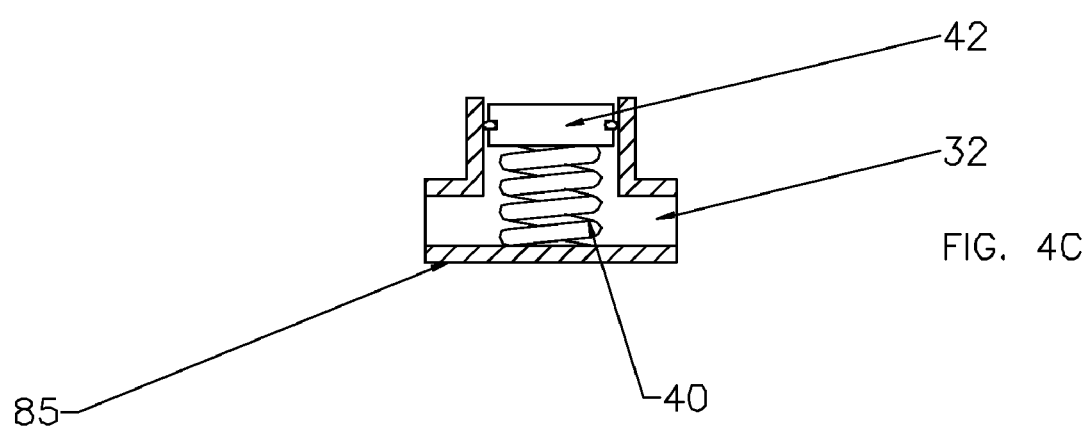

A reciprocating pump consists essentially of a piston moving back and forth in a cylinder and two one-way valves that control flow into and out of the cylinder. An embodiment of the present invention mitigates the inspection problem by providing a transparent viewport 20 (as shown in FIG. 2), and utilizing transparent tubing 21. Additionally inlet 66 and outlet 68 check-valves may be made of transparent material. Furthermore the preferred embodiment relocates these elements of the pump to visible areas of the fluid pathway. In this manner, the remaining pumping volume that cannot be readily inspected is reduced to the cylinder volume of the pump. The typical cylinder volume for the inexpensive pumps used in this embodiment is below the threshold of concern cited in infusion device standards.

Referring again to FIG. 2, the pumping system shown is illustrative of embodiments contemplated by the present invention, including the incorporation of reciprocating pumps 64, 80, in a reduced size and lower cost, single-use package, along with flow control devices (e.g., a shut off valve 76, a pulse damper 78, etc.), to alter the inherent flow characteristics of these reciprocating pumps. The reduced size allows the entire device to be placed within the confines of the sterile field of the operating room, thereby enabling the physician to personally monitor and/or control the pumping system.

Unlike many of the prior peristaltic-based pumping systems, the infusion 64 and aspiration pumps 80 of the present invention may be arranged in a single housing 23, along with the necessary tubing 84, 85 and valves 66, 68 (referring to FIGS. 6a and 6b) to supply and extract. In a preferred embodiment, the housing 23 may be of modular design, with one module containing the reciprocating pumps 64, 80, tubing 21, 84, 85 and valves 66, 68, 76, while a second module contains the required electronics and user interface to control the pumps and/or valves (not shown). This embodiment would facilitate sterilization of the system. Specifically, it may be the case that the pumps 64, 80, and valves 66, 68, 76, are best sterilized using gamma radiation. Electronic components, however, typically cannot be sterilized by gamma irradiation. With the modular design, the section containing the electronics could be separated from the rest of the pumping system and sterilized (using non radioactive methods (e.g., ethylene oxide).

The reciprocating, aspiration pump 80 as shown in FIG. 6b, may be used to aspirate fluid and any debris from the patient during medical intervention procedures, i.e. the pump 80 aspirates to remove any debris produced during diagnostics or procedures (e.g., angioplasty), by drawing the debris through a lumen, such as a catheter 72. The aspiration pump 80 is capable of matching or exceeding the rate of flow of the infusion pump 64 (see FIG. 6a), which need only provide enough flow to flush or agitate the lesion site. This imbalanced flow may be used to ensure that debris is evacuated from the patient, rather than being washed into the rest of the vascular system. By removing more liquid than is introduced, the net flow will have some blood traveling into the system, thereby carrying any debris produced with it. Of course, since blood will be removed from the patient, these flow rates must be controlled. In one embodiment, the flow rate of the aspiration pump 80 may be in the range of e.g., 40 to 200 mL/minute. The aspiration pump 80 may be a reciprocating piston pump, or more preferably a reciprocating diaphragm pump, such as that supplied by ACI Medical (San Marcos, Calif.), or other vendors, but may be any positive displacement pump that meets the requirements of low cost, and reduced size relative to a peristaltic pump with similar flow rates. In use, the aspiration pump 80 inlet is connected to a conduit suitable for extracting fluid from a patient, such as a guide catheter 72; the valve (if used) is connected to the aspiration pump 80 which is in turn connected to a conduit or flexible aspiration tubing 85 to route the fluid to an extraction bag 82 or container. The reciprocating, infusion pump 64 as shown in FIG. 6b is used to deliver fluid to the patient during the procedure, e.g., the infusion pump 64 provides an injection of fluid (e.g., saline, drugs, and/or contrast agent) into the procedure site (e.g., saphenous vein graft, carotid, etc.) to agitate any debris and allow visualization of the procedure. In one embodiment, the flow rate of the infusion pump 64 may be in the range of e.g., 20 to 50 mL/minute. The infusion pump 64 may be a reciprocating diaphragm pump, or alternatively may be a reciprocating piston pump, as discussed above.

In use, the flexible infusion tubing 84 is connected to the source of fluid e.g., the reservoir bag 62, to be injected, generally located approximately two feet above the infusion pump 64 to provide some positive head pressure to the pump. The outlet from the pump 64 is connected via conduit of flexible infusion tubing 84 to a means of injecting the fluid within the body, such as a flush catheter 70, which may be inserted 71 through a guide connector branch 74 into the inner diameter of the guide catheter 72, ultimately extending out of the end of the guide catheter 72 and into the procedure site (e.g., saphenous vein graft, carotid, etc.)

The aspiration pump 80 and the infusion pump 64 may contain a mechanism to allow the determination of the speed of the pump, such as an optical sensor to detect light reflected from a reflective surface of the rotating motor shaft, or alternatively, a sensor to detect fluctuating voltage, which is proportional to the speed of rotation of the shaft, or any other means of detecting pump rotation. In this manner, a control system may be utilized to monitor, maintain or alter the speed of the pumps, or alternatively activate an alarm if needed, e.g., in the event of a stalled motor.

There will be instantaneous speed variations of the pumps in response to unusual events or flow conditions. Unlike the peristaltic pumps, the positive displacement pumps are in intimate contact with the fluid, and are intended to be sized to provide sufficient flow to meet the system requirements. A blocked catheter will cause the pumps to stall and stop pumping until the blockage is cleared. This feature precludes the need for a pressure sensor as is required on the peristaltic system, because the pumps are not powerful enough to cause a significant and possibly dangerous pressure without stalling. Conversely, if the pumped fluid changes to gas, from liquid, the pumps will speed up significantly due to the greatly reduced load. Therefore, a control system is very adaptable to these embodiments.

The pumps' sensitivity to load variations is also helpful during the priming process. While air is being cleared through the pumps ahead of the liquid, the pumps will run relatively fast, then slow down significantly when the liquid has reached the pumping cylinders. The speed variation is detectable and can be used to signal to the operator that the pump is primed with liquid. The same speed variation would occur in reverse if a primed system experienced a large leak, resulting in an ingestion of air, causing the pumps to speed up. as previously discussed, this condition can be detected and used to initiate an alarm, for example.

The use of a typical embodiment of the pumping system of the present invention will now be described.

FIGS. 6a and 6b show fluid pathways. For convenience of illustration, the fluid pathway is schematically split into infusion, FIG. 6a, and extraction, FIG. 6b. Specifically, the fluid circuit path consists of reservoir bag 62, infusion pump 64, infusion pump inlet check-valve 66, infusion pump outlet check-valve 68, flush catheter 70, guide catheter 72, guide connector branch 74 having an injection branch 73, shut-off valve 76, pulse damper 78, aspiration pump 80 with internal inlet and exhaust check-valves (not shown), extraction bag 82, and flexible tubing for infusion 84 and aspiration 85, preferably of the transparent or translucent variety to transport the fluid from one of the above-described components to the next. Thus, during normal operation, fluid from reservoir bag 62 flows past infusion pump inlet check-valve 66 to infusion pump 64, where it is pumped past infusion pump outlet check-valve 68, through flexible infusion tubing 84 into the entrance portion of flush catheter 70. From there, the fluid flows out the distal end of the catheter 70 into the lesion or procedure site within the body of the patient that is to receive the diagnostic or therapeutic treatment. Simultaneously, or nearly so, fluid within the procedure site to be removed from the patient's body flows under pressure e.g., blood pressure, or applied vacuum, into the distal end of the guide catheter 72 (catheter 70 may be inserted into guide catheter 72 via guide connector branch 74), flowing through and exiting at the proximal end of the guide catheter, into the guide connector branch 74, and into flexible aspiration tubing 85. From there, the extracted fluid flows past or through the shut off valve 76, which may be incorporated into the damper valve 78 (as shown in FIG. 3), or it may be a unit separate from the damper valve 78, before flowing into aspiration pump 80, which may contain internal check-valves (not shown) or alternatively, external check-valves similar in operation to those of the infusion pump 64. Finally the fluid from the aspiration pump 80, flows through more flexible aspiration tubing 85 to be collected by extraction bag 82. The injection of contrast medium into an artery will now be described to more fully describe the operation of the pumping system of the present invention in an actual medical intervention.

Starting the Saline Infusion

After priming the pumps 64,80, or more preferably relying on the pumps 64,80 self priming capabilities, the saline reservoir bag 62 is located in an elevated position to avoid entraining air in the system, and the flush catheter 70 is now inserted onto the guidewire by techniques known in the art. This attachment procedure has the potential to trap a small air bubble at the tip, just inside the flush catheter 70. In this case, the fact that there is an open flow path through the infusion pump 64 serves to create a positive drip through the catheter 70 and expel the air bubble. The flush catheter 70 is now slid along the guidewire, and inside the guide catheter 72 to the lesion site (via guide connector branch 74). The pump process begins with the aspiration pump 80 running first for a set time period to establish a suction pressure prior to the infusion pump 64 turning on. The infusion pump 64 turns on at a flow rate significantly less than that of the aspiration pump, to assure that debris is not forced distal of the procedure site, rather than into the guide catheter 72.

In yet another embodiment, a distal balloon (not shown) may be used to create an area which may be vigorously flushed without allowing any debris to travel in the distal direction. Additionally, aspirating more fluid than is infused may keep debris from backing up into the artery (etc.) in the proximal direction.

Injecting the Contrast Medium

To inject the contrast medium, the flow of saline from the reservoir bag 62 is halted and the extraction side shut-off valve 76 is closed. Using an automated control system, these steps can be carried out nearly simultaneously. The syringe (not shown) containing the contrast medium is purged of air, and inserted into the injection port 73 of guide connector branch 74 located at the proximal end of the guide catheter 72. The plunger of the syringe is depressed, thereby injecting the contrast medium into the guide connector branch 74. Note that this injection port is in a direct flow path with the extraction side 75 of the guide connector branch 74. Thus, the shut-off valve 76 should be in the "closed" position; otherwise, the relatively low resistance offered by the extraction side 75 of the guide connector branch 74 compared to the "patient" side 77 of the guide connector branch 74, will likely cause most of the contrast medium to flow straight out of the guide connector branch 74, ultimately ending up in the extraction bag 82, rather than in the patient, where it is desired. When injection is complete, the syringe may either be left in the guide connector branch 74, or it may be withdrawn. When the contrast has diffused sufficiently to where its visualization assistance is needed, the pumping system may be re-energized in the same sequence as described previously.

When the medical diagnostic or therapeutic treatment is complete, the pumps are de-energized, starting first with the infusate pump 64. The extraction side shut-off valve 76 is closed. The catheter 70 is withdrawn from the patient's body. The saline solution is drained or pumped into the extraction bag 82, clearing the lines. The liquid flow circuit is then disassembled, and the pump system may be discarded. Components that are to be re-used, if any, are cleaned and sterilized.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A method for infusing and aspirating fluids into and out of a living being, comprising:
   (a) providing a pumping system comprising:
      (i) a means of infusing a liquid into said patient;
      (ii) a means of aspirating a fluid from said patient, each of said means comprising a positive displacement pump other than a peristaltic type pump, said positive displacement pump having an inlet and an outlet side;
      (iii) an aspiration pathway containing a fluid consisting essentially of liquid during use;
      (iv) a shut-off valve located on said inlet side of said aspirating means pump, said shut-off valve arranged to close off a pathway of said liquid when the pump is stopped; and
      (v) means for controlling said pumps;
   (b) connecting said infusion pathway and said aspiration pathway to said living being to create a fluid circuit;
   (c) first energizing said aspirating means; and
   (d) subsequently energizing said infusing means such that a flow rate of infusate is less than a flow rate of aspirate.

2. The method of claim 1, wherein said pumping system further comprises means for independently controlling the fluid pressure or volume on the infusion and extraction sides.

3. The method of claim 1, wherein said pumping system is capable of maintaining a continuous fluid path from the infusate pumping means through the patient and out to the aspirating pumping means, when said pumping means is operating as well as sitting idle.

4. The method of claim 1, wherein said pumping system is capable of self-priming.

5. The method of claim 1, wherein said pumping system further comprises visual air bubble detection.

6. The method of claim 5, wherein said air bubble detection comprises viewports located in the fluid path.

7. The method of claim 6, wherein said viewport locations include pumps and valves.

8. The method of claim 1, wherein said infusion means and said aspiration means are provided by a single pump.

9. The method of claim 1, wherein said infusion means and said extraction means are provided by separate pumps.

10. The method of claim 1, wherein said infusion means comprises a piston pump.

11. The method of claim 1, wherein said extraction means comprises a diaphragm pump.

12. The method of claim 9, wherein said pumps are driven by motors comprising speed sensors.

13. The method of claim 12, wherein said speed sensors comprise electrical outputs, and said electrical outputs are used in a negative feedback loop to adjust said speed of said motors.

14. The method of claim 12, wherein said speed sensors comprise electrical outputs, and said electrical outputs are used by a control system to stop one or both of said motors if an alarm condition is sensed.

15. The method of claim 1, wherein said pumping system further comprises a damper apparatus located on the extraction side of the fluid circuit.

16. The method of claim 1, wherein said shut-off valve also functions as said damper apparatus.

17. The method of claim 1, wherein said controlling means is readily removable from said infusing and aspirating means.

18. The method of claim 1, wherein said shut-off valve is arranged to close off a flow of fluid when said infusing means is stopped.

19. The method of claim 1, wherein said means for controlling said pumps comprises a user interface for inputting commands to said controlling means.

20. The method of claim 1, wherein said fluids are infused and aspirated simultaneously.

* * * * *